US012622697B2

(12) United States Patent
Baril et al.

(10) Patent No.: US 12,622,697 B2
(45) Date of Patent: May 12, 2026

(54) SURGICAL STAPLING DEVICE WITH FIRING LOCKOUT MEMBER

(71) Applicant: Covidien LP, Mansfield, MA (US)

(72) Inventors: Jacob C. Baril, Norwalk, CT (US); Kenneth H. Whitfield, North Haven, CT (US); Roanit Arthur Fernandes, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/870,995

(22) PCT Filed: May 23, 2023

(86) PCT No.: PCT/IB2023/055293
§ 371 (c)(1),
(2) Date: Dec. 2, 2024

(87) PCT Pub. No.: WO2023/233242
PCT Pub. Date: Dec. 7, 2023

(65) Prior Publication Data
US 2025/0325266 A1      Oct. 23, 2025

Related U.S. Application Data

(60) Provisional application No. 63/348,569, filed on Jun. 3, 2022.

(51) Int. Cl.
*A61B 17/072* (2006.01)
(52) U.S. Cl.
CPC ................... *A61B 17/07207* (2013.01); *A61B 2017/07271* (2013.01); *A61B 2017/07278* (2013.01); *A61B 2017/07285* (2013.01)

(58) Field of Classification Search
CPC ............ A61B 17/072; A61B 17/07207; A61B 2017/07271; A61B 2017/07278; A61B 2017/07285
(Continued)

(56) References Cited

U.S. PATENT DOCUMENTS 11,666,330 B2 * 6/2023 Whitfield ............. A61B 17/072
227/175.2
2013/0098966 A1 * 4/2013 Kostrzewski .... A61B 17/07207
606/1
(Continued)

FOREIGN PATENT DOCUMENTS

CN 111616763 * 9/2020
EP 2586382 A2 5/2013
EP 2777532 A2 9/2014

OTHER PUBLICATIONS

PCT/IB2023/055293, The International Search Report and Written Opinion, mailed Aug. 31, 2023, 12pgs.

*Primary Examiner* — Linda J. Hodge

(57) ABSTRACT

A surgical stapling device includes a tool assembly having an anvil assembly and a cartridge assembly, and a drive assembly. The cartridge assembly includes a staple cartridge having an actuation sled assembly and channel member that supports a lockout member. The lockout member includes a stop member that interacts with the drive assembly when the actuation sled assembly is not present within a proximal portion of the staple cartridge to prevent advancement of the drive assembly and firing of the stapling device.

20 Claims, 12 Drawing Sheets

(58) Field of Classification Search
USPC ................................ 227/175.2, 175.3, 175.4
See application file for complete search history.

(56) References Cited

U.S. PATENT DOCUMENTS

2015/0272576 A1 *  10/2015  Cappola ............... A61B 17/072
                                                        227/175.2
2015/0374363 A1 *  12/2015  Laurent, IV ......... A61B 17/105
                                                        227/176.1
2016/0058446 A1 *   3/2016  Shelton, IV ..... A61B 17/07207
                                                        227/176.1
2021/0307743 A1    10/2021  Cappola et al.

* cited by examiner

SURGICAL STAPLING DEVICE WITH FIRING LOCKOUT MEMBER

CROSS-REFERENCE TO RELATED APPLICATIONS

This application is a National Stage Application of PCT/IB2023/055293 filed May 23, 2023, which claims benefit of and priority to U.S. Provisional Application No. 63/348,569 filed Jun. 3, 2022, and the disclosures of each of the above-identified applications are hereby incorporated by reference in their entirety.

FIELD

The disclosure is directed to surgical stapling devices and, more particularly, to surgical stapling devices having lockout mechanisms to prevent firing of the stapling device when the stapling device has a spent staple cartridge or when an actuation sled is not present in the staple cartridge.

BACKGROUND

Surgical stapling devices for simultaneously stapling and cutting tissue are well known in the art and include a tool assembly and a drive assembly. The tool assembly includes an anvil assembly and a cartridge assembly that are movable in relation to each other between open and clamped positions. The cartridge assembly has a channel member and a staple cartridge that is received within the channel member. Typically, the staple cartridge includes a cartridge body that supports staples, pushers, and an actuation sled, and the actuation sled is movable through the cartridge body from a retracted position to an advanced position into sequential engagement with the pushers to sequentially eject the staples from the cartridge body.

In some stapling devices, a knife is supported on the actuation sled and is movable with the actuation sled through the cartridge body. The drive assembly is positioned proximally of the actuation sled and is movable in relation to the anvil and cartridge assemblies to advance the actuation sled and knife through the staple cartridge to move the tool assembly between open and clamped positions, to eject the staples from the cartridge body, and to cut tissue clamped between the anvil and cartridge assemblies. When a stapling device is fired with a spent staple cartridge or a staple cartridge that does not have an actuation sled present in the staple cartridge, staples will not be ejected from the staple cartridge. As such, cut tissue will not be sutured.

A continuing need exists for a lockout of simple construction that can prevent advancement of a drive assembly of a stapling device through the staple cartridge when a sled is not present in a proximal portion of the staple cartridge.

SUMMARY

This disclosure is directed to a surgical stapling device includes a tool assembly having an anvil assembly, a cartridge assembly, and a drive assembly. The cartridge assembly includes a staple cartridge having an actuation sled assembly and channel member that supports a lockout member. The lockout member includes a stop member that interacts with the drive assembly when the actuation sled assembly is not present within a proximal portion of the staple cartridge to prevent advancement of the drive assembly and firing of the stapling device.

Aspects of the disclosure are directed to a surgical stapling device including an elongate body, a tool assembly, a drive assembly, and a lockout member. The elongate body has a proximal portion and a distal portion. The tool assembly is supported on the distal portion of the elongate body and includes an anvil assembly and a cartridge assembly. The anvil assembly has a staple forming surface that defines a first knife slot. The cartridge assembly is coupled to the anvil assembly to facilitate movement of the tool assembly between open and clamped positions and includes a channel member and a staple cartridge. The channel member has side walls and a bottom wall that defines a channel. The bottom wall defines a second knife slot. The staple cartridge is supported within the channel of the channel member and includes a cartridge body, staples, pushers, and an actuation sled assembly. The cartridge body has a tissue engaging surface and defines a third knife slot and staple receiving slots positioned on each side of the third knife slot. The staples are received in the staple receiving slots. The actuation sled assembly is movable within the cartridge body from a sled retracted position to a sled advanced position to eject the staples from the staple receiving slots of the cartridge body. The actuation sled assembly includes an actuation sled and a knife secured to the actuation sled. The actuation sled has a fin that extends through the second knife slot to a position outwardly of the channel. The knife includes a knife blade having a cutting edge positioned within and extending above the tissue engaging surface of the cartridge body. The drive assembly includes a working member that is positioned proximally of the actuation sled assembly and is movable through the cartridge body between retracted and advanced positions to advance the actuation sled assembly from the sled retracted position to the sled advanced position. The lockout member is supported on an outer surface of the channel member and is movable from a first position obstructing movement of the working member from the retracted position to the advanced position and a second position allowing movement of the working member from the retracted position to the advanced position. The fin of the actuation sled is positioned to engage the lockout member when the actuation sled assembly is moved from the sled retracted position towards the sled advanced position to move the lockout member from the first position to the second position.

In aspects of the disclosure, the lockout member includes a stop member that extends across the second knife slot, and the fin of the actuation sled is positioned to engage the stop member to move the lockout member from the first position to the second position.

In some aspects of the disclosure, the fin has an angled distal cam surface and a proximal stop surface, and the angled distal cam surface is configured to move the lockout member from the first position to the second position.

In certain aspects of the disclosure, the lockout member includes a lance that extends distally from the stop member, and the lance is positioned to engage the proximal stop surface of the fin to prevent movement of the actuation sled assembly to the sled retracted position.

In aspects of the disclosure, the actuation sled assembly includes a retraction link that is movable from a first position to a second position in response to movement of the actuation sled assembly from the sled retracted position towards the sled advanced position to couple the actuation sled assembly to the working member of the drive assembly.

In some aspects of the disclosure, the retraction link includes a protrusion, the drive assembly defines an opening, and the protrusion is received within the opening when the retraction link is in the second position.

In certain aspects of the disclosure, the working member includes first and second beams and a vertical strut connecting the first beam to the second beam, and the vertical strut is movable through the first, second, and third knife slots as the working member moves between the retracted and advanced positions.

In aspects of the disclosure, the first beam includes a proximally facing cam slot that is positioned to engage the lance when the working member moves from the advanced position to the retracted position to move the lockout member from the first position to the second position.

In some aspects of the disclosure, the first beam includes a distally facing cutout that is positioned adjacent the fin of the actuation sled to allow the lance to engage the stop surface of the fin.

In certain aspects of the disclosure, the stapling device includes a handle assembly coupled to the proximal portion of the elongate body.

Other aspects of the disclosure are directed to a tool assembly that includes an anvil assembly, a cartridge assembly, a drive assembly, and a lockout member. The anvil assembly has a staple forming surface that defines a first knife slot. The cartridge assembly is coupled to the anvil assembly to facilitate movement of the tool assembly between open and clamped positions and includes a channel member and a staple cartridge. The channel member has side walls and a bottom wall that define a channel. The bottom wall defines a second knife slot. The staple cartridge is supported within the channel of the channel member and includes a cartridge body, staples, pushers, and an actuation sled assembly. The cartridge body has a tissue engaging surface and defines a third knife slot and staple receiving slots positioned on each side of the third knife slot. The staples are received in the staple receiving slots. The actuation sled assembly is movable within the cartridge body from a sled retracted position to a sled advanced position to eject the staples from the staple receiving slots of the cartridge body. The actuation sled assembly includes an actuation sled and a knife secured to the actuation sled. The actuation sled has a fin that extends through the second knife slot to a position outwardly of the channel, and the knife includes a knife blade having a cutting edge positioned within and extending above the tissue engaging surface of the cartridge body. The drive assembly includes a working member that is positioned proximally of the actuation sled assembly and is movable through the cartridge body between retracted and advanced positions to advance the actuation sled assembly from the sled retracted position to the sled advanced position. The lockout member is supported on an outer surface of the channel member and is movable from a first position obstructing movement of the working member from the retracted position to the advanced position to a second position allowing movement of the working member from the retracted position to the advanced position. The fin of the actuation sled is positioned to engage the lockout member when the actuation sled assembly is moved from the sled retracted position towards the sled advanced position to move the lockout member from the first position to the second position.

Other aspects of the disclosure are directed to a cartridge assembly that includes a channel member, a staple cartridge, and a lockout member. The channel member has side walls and a bottom wall that define a channel, and the bottom wall defines a first knife slot. The staple cartridge is supported within the channel of the channel member and includes a cartridge body, staples, pushers, and an actuation sled assembly. The cartridge body has a tissue engaging surface and defines a second knife slot and staple receiving slots positioned on each side of the second knife slot. The staples are received in the staple receiving slots. The actuation sled assembly is movable within the cartridge body from a sled retracted position to a sled advanced position to eject the staples from the staple receiving slots of the cartridge body. The actuation sled assembly includes an actuation sled and a knife secured to the actuation sled. The actuation sled has a fin that extends through the second knife slot to a position outwardly of the channel, and the knife includes a knife blade having a cutting edge positioned within and extending above the tissue engaging surface of the cartridge body. The lockout member is supported on an outer surface of the channel member of the cartridge assembly and has a stop member that extends across the first knife slot. The lockout member is movable from a first locked position to a second unlocked position in response to movement of the actuation sled assembly from the sled retracted position towards the sled advanced position.

Other features of the disclosure will be appreciated from the following description.

BRIEF DESCRIPTION OF THE DRAWINGS

Various aspects of the disclosure are described herein below with reference to the drawings, wherein.

DETAILED DESCRIPTION

Figure 1:
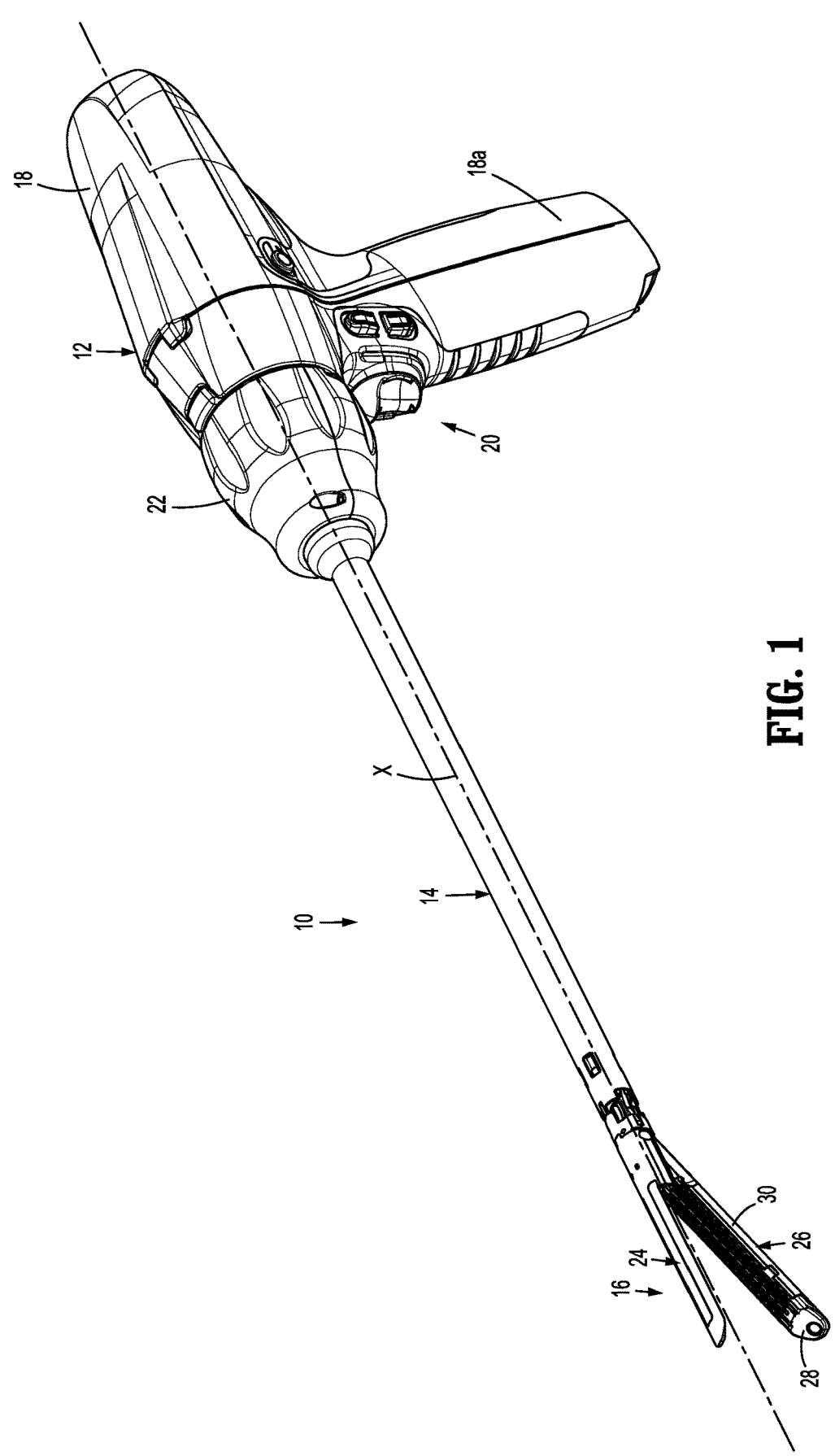
FIG. 1 is side perspective view of a stapling device according to aspects of the disclosure including a tool assembly in an open position.

The disclosed surgical stapling device will now be described in detail with reference to the drawings in which like reference numerals designate identical or corresponding elements in each of the several views. However, it is to be understood that aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the stapling device in its customary manner, while the term "distal" is used generally to refer to that portion of the device that is farther from the clinician during use of the stapling device in its customary manner. In addition, the term "clinician" is used generally to refer to medical personnel including doctors, nurses, and support personnel. Further, directional terms such as front, rear, upper, lower, top, bottom, and similar terms are used to assist in understanding the description and are not intended to limit the disclosure.

The disclosed surgical stapling device includes a tool assembly having an anvil assembly, a cartridge assembly, and a drive assembly. The cartridge assembly has a channel member that defines a channel and a staple cartridge that is received within the channel. The staple cartridge includes a cartridge body, staples, pushers, and an actuation sled assembly. The drive assembly has a working member that is movable through the tool assembly to advance the actuation sled assembly through the staple cartridge to actuate the tool assembly. The cartridge assembly supports a lockout member that interacts with the drive assembly when the actuation sled is not present within a proximal portion of the staple cartridge to prevent advancement of the drive assembly and firing of the stapling device.

FIG. 1 illustrates a surgical stapling device according to aspects of the disclosure shown generally as stapling device

10. The stapling device 10 includes a handle assembly 12, an elongate body 14, and a tool assembly 16. The elongate body 14 defines a longitudinal axis "X" (FIG. 1). The handle assembly 12 includes a body 18 that defines a hand grip 18*a*, a plurality of actuator buttons 20, and a rotation knob 22. The rotation knob 22 is rotatably supported on a distal portion of the body 18 of the handle assembly 12 and supports the elongate body 14 to facilitate rotation of the elongate body 14 and the tool assembly 16 about the longitudinal axis "X" of the elongate body 14 in relation to the handle assembly 12. The actuator buttons 20 control operation of the various functions of the stapling device 10 including articulation, clamping, firing, and cutting of tissue.

Figures 11, 12:
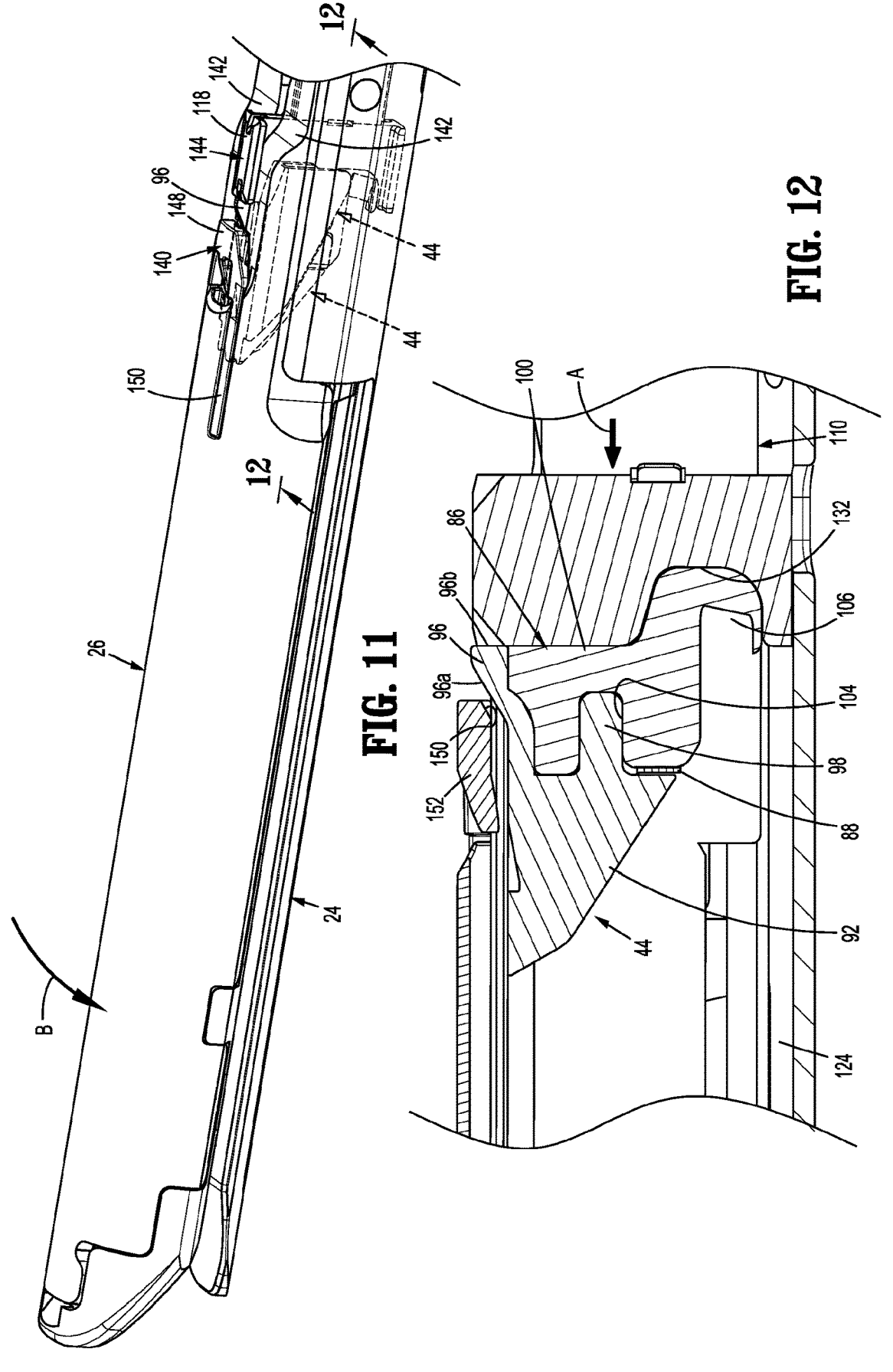
FIG. 11 is a side perspective view of the tool assembly of the stapling device shown in FIG. 1 with the tool assembly in a clamped position with the actuation sled assembly present in the staple cartridge.
FIG. 12 is a cross-sectional view taken along section line 12-12 of FIG. 11.

The tool assembly 16 includes an anvil assembly 24 and a cartridge assembly 26 that are movable in relation to each other between an open position (FIG. 1) and a clamped position (FIG. 11). In aspects of the disclosure, the anvil assembly 24 is fixed in relation to the elongate body 14 and the cartridge assembly 26 is pivotable towards and away from the anvil assembly 24. However, it is envisioned that the cartridge assembly 26 could be fixed in relation to the elongate body 14 and the anvil assembly 24 could pivot towards and away from the cartridge assembly 26. Although the stapling device 10 is illustrated as an electrically powered stapling device, it is envisioned that the tool assembly 16 would also be suitable for use with manually powered surgical stapling devices and robotically operated stapling systems. U.S. Pat. No. 9,055,943 discloses a surgical stapling device including a powered handle assembly, U.S. Pat. No. 6,241,139 discloses a surgical stapling device including a manually actuated handle assembly, and U.S. Pat. No. 9,962,159 discloses a stapling device that is configured for use with a robotic system.

Figures 2, 3:
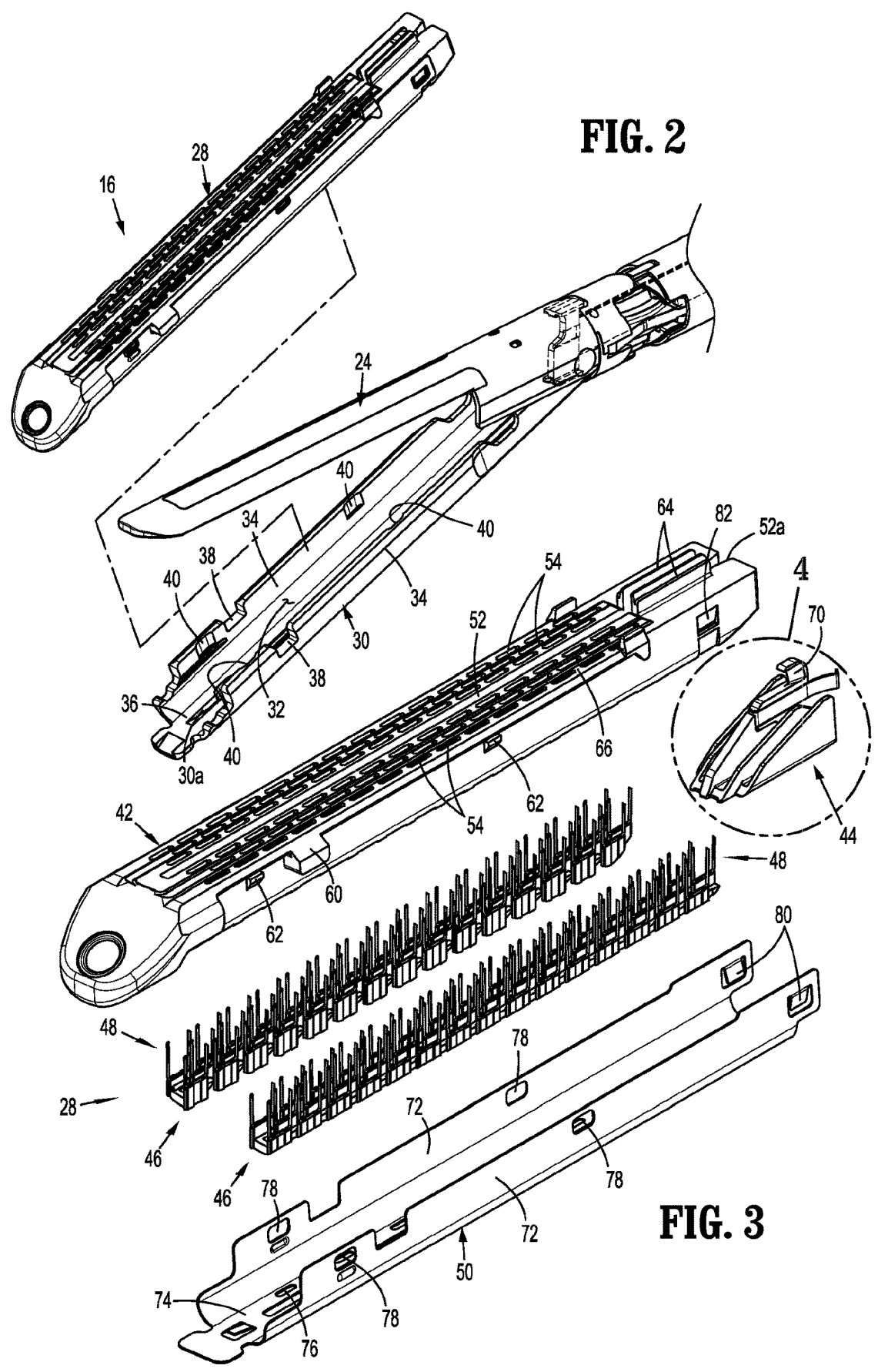
FIG. 2 is a side perspective from above of a distal portion of the stapling device shown in FIG. 1 illustrating an anvil and a cartridge assembly of the tool assembly in the open position with a staple cartridge removed from a channel of the cartridge assembly.
FIG. 3 is an exploded, side perspective view of the staple cartridge of the cartridge assembly shown in FIG. 2.
Figure 7:
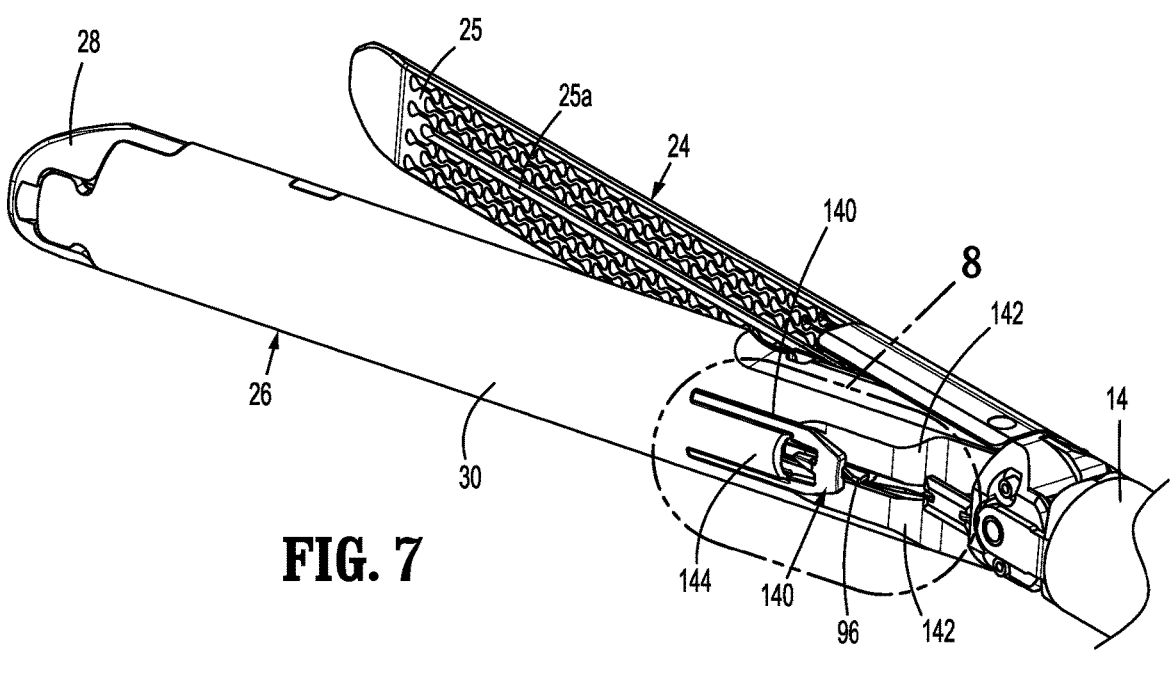
FIG. 7 is a bottom perspective view of the tool assembly shown in FIG. 2 with the staple cartridge received in the channel of the cartridge assembly.
Figure 8:
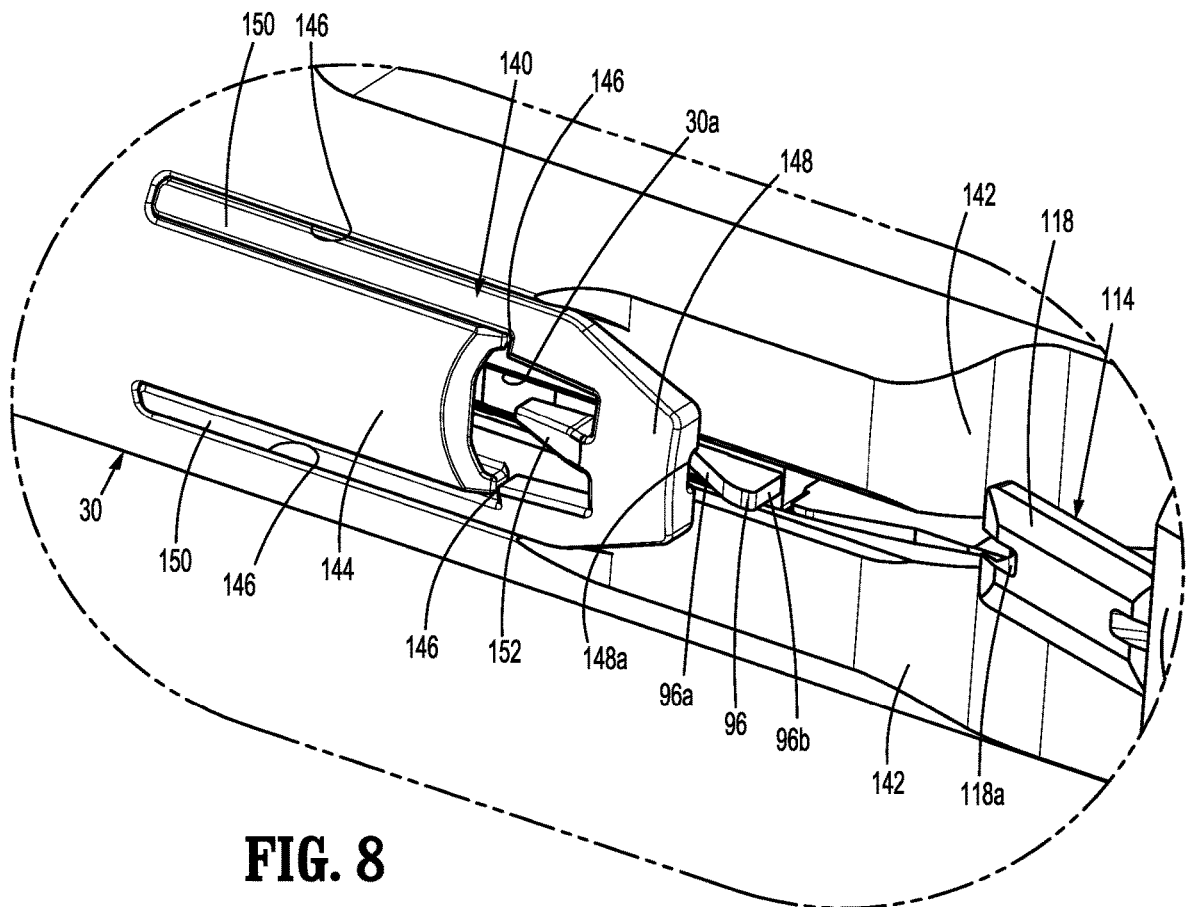
FIG. 8 is an enlarged view of the indicated area of detail shown in FIG. 7.
Figure 9:
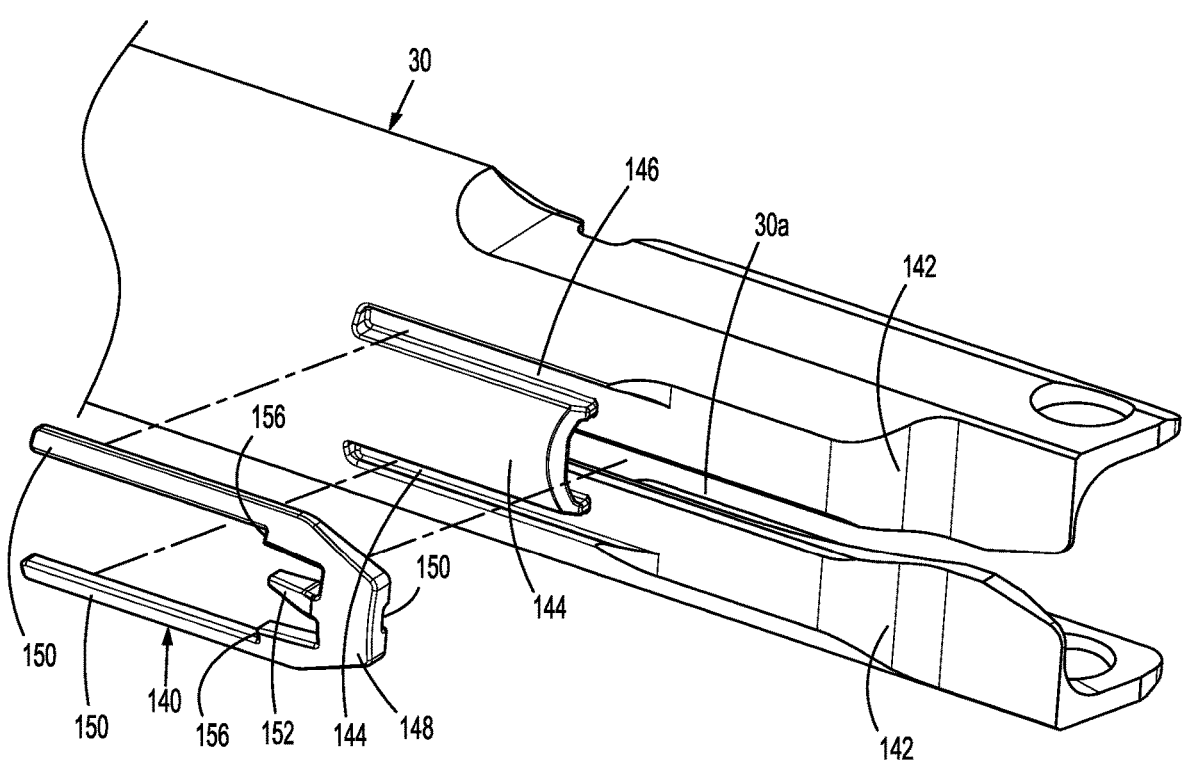
FIG. 9 is a perspective view of a proximal portion of the channel of the cartridge assembly shown in FIG. 7 with a lockout member separated from the channel.
Figure 10:
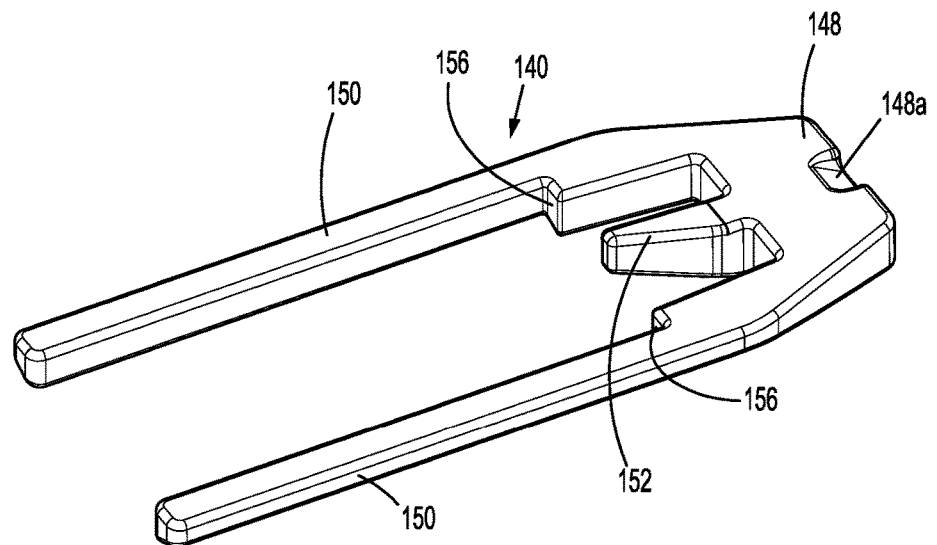
FIG. 10 is a side perspective view of the lockout member shown in FIG. 9.

FIGS. 2 and 3 illustrate the tool assembly 16 which includes the anvil assembly 24 and the cartridge assembly 26 (FIG. 1). The anvil assembly 24 includes a staple forming surface 25 that defines a knife slot 25*a* (FIG. 7). The cartridge assembly 26 includes a staple cartridge 28 and a channel member 30 that defines a channel 32 that receives the staple cartridge 28. In aspects of the disclosure, the staple cartridge 28 is releasably secured within the channel 32 to facilitate reuse of the stapling device 10. The channel member 30 includes side walls 34 and a bottom wall 36 that define the channel 32. The bottom wall 36 defines a knife slot 30*a*. In aspects of the disclosure, the side walls 34 of the channel member 30 define cutouts 38 and notches 40 that are provided to align and retain the staple cartridge 28 within the channel 32 of the channel member 30 as described in further detail below.

The staple cartridge 28 includes a cartridge body 42, an actuation sled assembly 44, pushers 46, staples 48, and a base plate 50. The cartridge body 42 defines a knife slot 52 and staple receiving slots 54 positioned on opposite sides of the knife slot 52. The knife slot 52 in the cartridge body 42 is longitudinally aligned with the knife slot 30*a* of the channel member 30 when the staple cartridge 28 is received in the channel 32 of the channel member 30. In aspects of the disclosure, the staple receiving slots 54 are aligned in rows on each side of the knife slot 52. Although three rows of staple receiving slots 54 are shown on each side of the knife slot 52, it is envisioned that the cartridge body 42 may define one or more rows of staple receiving slots 54 on each side of the knife slot 52. Each of the staple receiving slots 54 receives one of the staples 48 and one of the pushers 46. The pushers 46 support the staples 48 and are sequentially engaged by the actuation sled assembly 44 as the actuation sled assembly 44 is advanced through the cartridge body 42 from a retracted position to an advanced position to eject the staples 48 from the cartridge body 42. The base plate 50 is secured to a bottom of the cartridge body 42 to prevent the pushers 46 and the staples 48 from falling from the bottom of the cartridge body 42.

In aspects of the disclosure, the cartridge body 42 includes outwardly extending protrusions 60 that are received within the cutouts 38 in the side walls 34 of the channel member 30 to properly position the staple cartridge 28 within the channel 32 of the channel member 30. In certain aspects of the disclosure, the cartridge body 42 also includes tabs 62 that are received in the notches 40 in the side walls 34 of the channel member 30 to releasably retain the staple cartridge within the channel 32 of the channel member 30. In some aspects of the disclosure, the cartridge body 42 includes raised guards 64 that extend above a tissue engaging surface 66 of the cartridge body 42 on opposite sides of a proximal portion of the knife slot 52 at a position proximal of the staple receiving slots 54. The raised guards 64 shield a knife 86 of the actuation sled assembly 44 when the actuation sled assembly 44 is in a sled retracted position as described in further detail below.

The base plate 50 of the staple cartridge 28 includes side walls 72 and a bottom wall 74 that define a channel that receives the cartridge body 42 of the staple cartridge 28. The bottom wall 74 of the base plate 50 defines a knife slot 76 that is longitudinally aligned with the knife slots 52 and 30a of the cartridge body 42 and the channel member 30, respectively. The side walls 72 of the base plate 50 define openings 78 that receive the tabs 62 of the cartridge body 42 in snap-fit fashion to secure the base plate 50 to the cartridge body 42. In aspects of the disclosure, the proximal portion of the side walls 72 of the base plate 50 also includes inwardly extending resilient fingers 80 that snap into notches 82 in the cartridge body 42 to secure the base plate 50 to the cartridge body.

Figure 4:
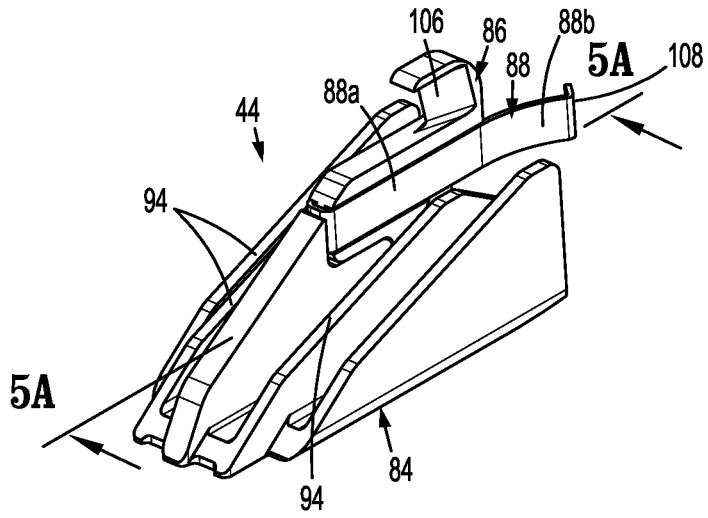
FIG. 4 is an enlarged view of the indicated area of detail shown in FIG. 3 illustrating an actuation sled assembly.
Figure 5:
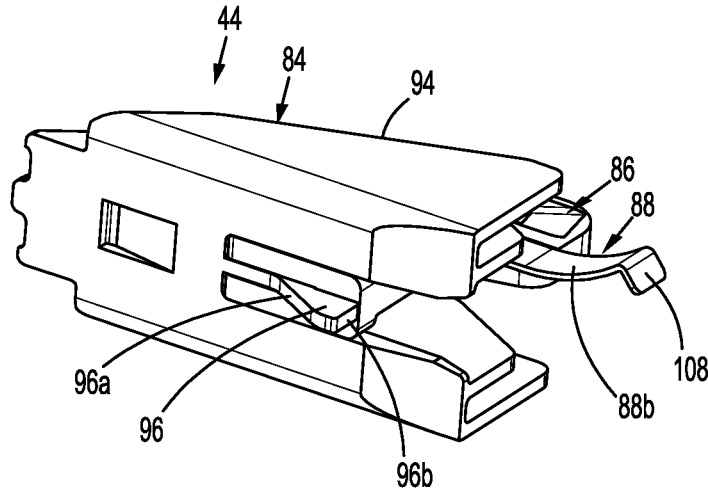
FIG. 5 is a bottom perspective view of the actuation sled assembly shown in FIG. 4.
Figures 5A, 6:
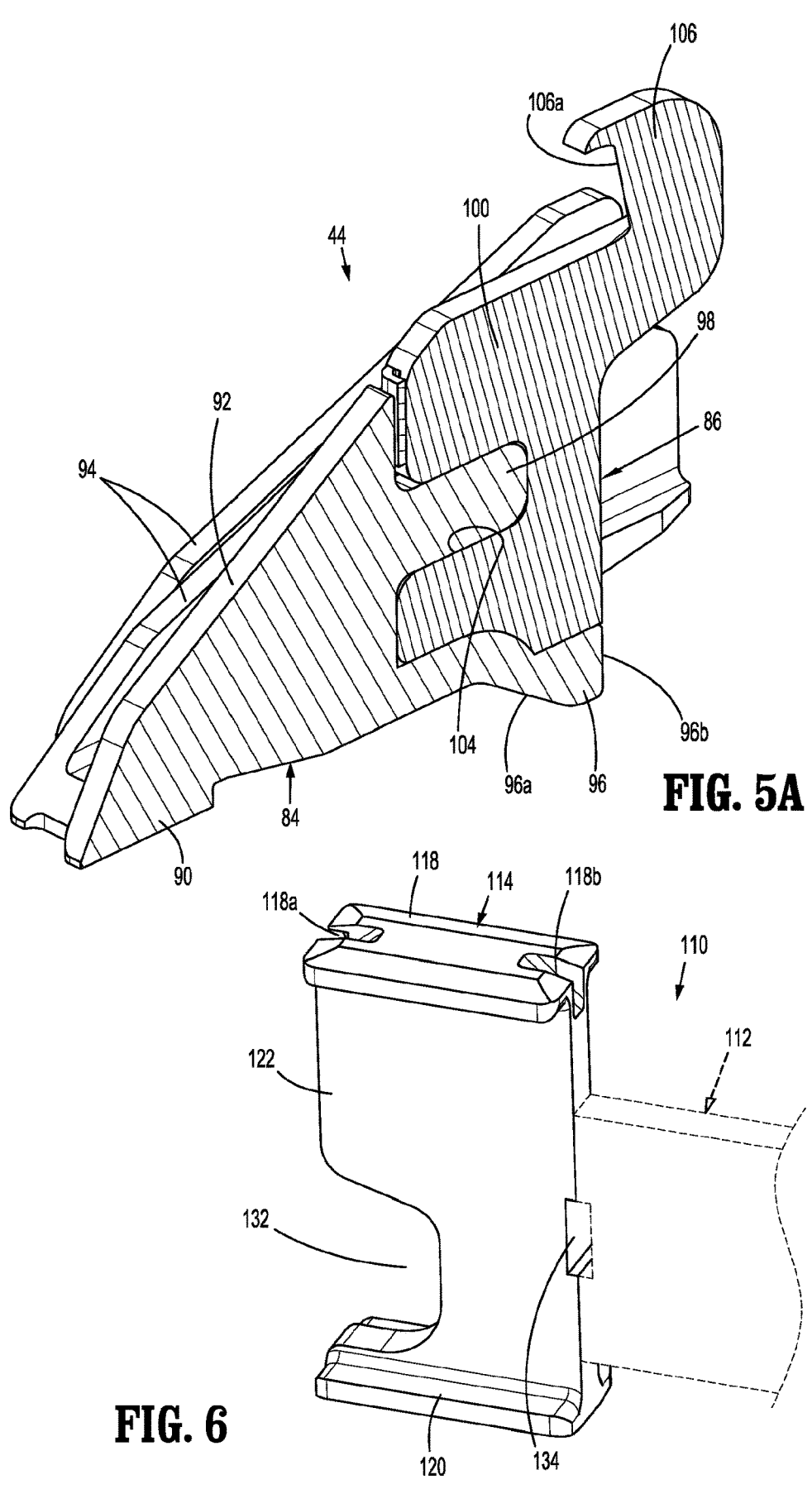
FIG. 5A is a cross-sectional view taken along a longitudinal axis of a central portion of the actuation sled assembly.
FIG. 6 is a side perspective view of a working member of a drive assembly of the stapling device shown in FIG. 1.

FIGS. 4-5A illustrate the actuation sled assembly 44 which includes an actuation sled 84, a knife 86, and a retraction link 88. The actuation sled 84 includes a sled body 90 that has a central portion 92 and cam surfaces 94 that are positioned on opposite sides of the central portion 92 of the sled body 90. The cam surfaces 94 define ramps that are positioned to engage the pushers 46 (FIG. 3) as the actuation sled 84 moves from the sled retracted position towards a sled advanced position to sequentially eject the staples 48 (FIG. 3) from the cartridge body 42 of the staple cartridge 28. The central portion 92 of the sled body 90 of the actuation sled 84 is received within the knife slot 52 of the cartridge body 42 and includes a lower fin 96 that extends through the knife slot 76 of the base plate 50 and through the knife slot 30a of the channel member 30 (FIG. 2). The fin 96 includes an angled distal cam surface 96a and a substantially vertical proximal stop surface 96b. The central portion 92 of the body 90 of the actuation sled 84 also includes a proximal extension 98 (FIG. 5A) that is secured to the knife 86. In aspects of the disclosure, the actuation sled 84 is formed from plastic, the knife 86 is formed from metal, e.g., stainless steel, and the actuation sled 84 is over molded to the knife 86. Alternately, other techniques and securement means are envisioned to secure the knife 86 to the actuation sled 84.

The knife 86 includes a body 100 and a knife blade 106. The body 100 of the knife 86 defines a centrally located pocket 104 (FIG. 5A) that receives the proximal extension 98 of the actuation sled 84 to secure the knife 86 to the actuation sled 84. The knife blade 106 has a cutting edge 106a (FIG. 5A) and extends upwardly and proximally from the body 100 of the knife 86 such that the cutting edge 86a extends upwardly from the knife slot 52 of the cartridge body 42 (FIG. 3) to a position above the tissue engaging surface 66 (FIG. 3) of the cartridge body 42 of the staple cartridge 28. When the actuation sled assembly 44 is in a retracted position in the cartridge body 42 of the staple cartridge 28, the cutting edge 106a of the knife blade 106 is positioned between the raised guards 64 of the cartridge body 42 proximally of the body 100 of the knife 86.

The retraction link 88 of the actuation sled assembly 44 is formed of a resilient material, e.g., spring steel, and includes a longitudinal portion 88a and a curved portion 88b. The longitudinal portion 88a is secured to the body 100 of the knife 86 and the curved portion 88b extends proximally from the longitudinal portion 88a to a position proximal of the knife 86. In aspects of the disclosure, the body 100 of the knife 86 may include a longitudinal groove (not shown) that receives the longitudinal portion 88a of the retraction link 88. The curved portion 88b of the retraction link 88 has a proximal end that includes or supports a bend or protrusion 108. The retraction link 88 is received within and moves through the knife slot 52 of the cartridge body 42 when the actuation sled assembly 44 moves from the sled retracted position towards the sled advanced position. When the actuation sled assembly 44 is in the sled retracted position, the curved portion 86b of the retraction link 88 is positioned within a recess 91 (FIG. 18A) defined within the cartridge body 42 in a non-deformed configuration. When the actuation sled assembly 44 is moved from the sled retracted position towards the sled advanced position, the curved portion 88b of the retraction link 88 moves from within the recess 91 into the knife slot 52 and is deformed inwardly into substantial longitudinal alignment with the distal portion 88a of the retraction link 88 to move the bend or protrusion 108 inwardly into longitudinal alignment with the body 100 of the knife 86.

FIG. 6 illustrates a drive assembly 110 of the stapling device 10 (FIG. 1). The drive assembly 110 includes a resilient and/or flexible drive beam 112 and a working member 114. The drive beam 112 has a proximal portion (not shown) that is coupled to a drive rod (not shown) supported within the elongate body 14 of the stapling device 10 (FIG. 1) and a distal portion 112a that is coupled to the working member 114. In aspects of the disclosure, the resilient drive beam 112 is formed from laminated sheets of material, e.g., steel, that are welded to the working member 114. Alternately other materials of construction and securement techniques are envisioned.

The working member 114 of the drive assembly 110 has an I-beam configuration and includes a first beam 118, a second beam 120, and a vertical strut 122 that connects the first beam 118 to the second beam 120. The working member 114 is positioned proximally of the actuation sled assembly 44 (FIG. 4) and is movable, in response to activation of the actuation buttons 20 (FIG. 1), through the tool assembly 16 between retracted and advanced positions to move the actuation sled assembly 44 through the tool assembly 16 (FIG. 1) from the sled retracted position to sled advanced position. As the working member 114 moves through the cartridge assembly 26, the first beam 118 of the working member 114 is received within a channel 124 (FIG. 12) defined within the anvil assembly 24, the second beam 120 is engaged with the channel member 30 of the cartridge assembly 26, and the vertical strut 122 moves through the knife slots 52 and 30a of the cartridge body 42 and the channel member 30 of the cartridge assembly 28 (FIG. 3) and the knife slot 25a (FIG. 12) of the anvil assembly 24. In aspects of the disclosure, the first beam 118 of the working member 114 defines a distally facing cutout 118a and a proximally facing cam slot 118b that are aligned with the knife slot 30a in the channel member 30.

In aspects of the disclosure, the vertical strut 122 of the working member 114 defines a distally facing concavity 132 and a proximally facing recess or opening 134. The distally facing cavity 132 receives the portion of the knife 86 that includes the knife blade 106 when the working member 114 of the drive assembly 110 is moved into engagement with the actuation sled assembly 44 (FIG. 12) such that the working member 114 of the drive assembly 110 is in abutting relation with the actuation sled assembly 44. The opening 134 receives the bend or protrusion 108 of the retraction link 88 when the curved portion 86b of the retraction link 88 is deformed inwardly to couple the actuation sled assembly 44 to the working member 114. The retraction link 88 couples the actuation sled assembly 44 to the working member 114 such that retraction of the drive assembly 110 after the stapling device 10 (FIG. 1) has been fired also retracts the actuation sled assembly 44.

FIGS. 7-10 illustrate a lockout member 140 of the tool assembly 16 (FIG. 1). The lockout member 140 is secured to a proximal portion of the channel member 30 of the cartridge assembly 26 (FIG. 1) and is formed from a resilient material such as spring steel or the like. In aspects of the disclosure, the lockout member 140 can be formed in a variety of manners and processes including stamping, metal injection molding (MIM), etc. The thickness of the lockout member 140 can be selectively chosen to provide a desired degree of rigidity or flexibility. The proximal portion of the channel member 30 includes ramps 142 that are positioned on each side of the knife slot 30a and are engaged by the first beam 118 of the working member 114. The channel member 30 includes an outer surface that includes an overhang 144 that is defined by spaced elongate slots 146 in the channel member 30. The overhang 144 is positioned distally of the ramps 142. The lockout member 140 is substantially U-shaped and includes a stop member 148 and two legs 150 that extend distally from the stop member 148. The legs 150 are secured within the elongate slots 146 of the channel member 30 such as by welding such that the stop member 148 of the lockout member 140 is supported on the channel member 30 in cantilevered fashion with the stop member 148 extending across the knife slot 30a of the channel member 30.

The stop member 148 of the lockout member 140 includes a proximal surface that defines an angled cam surface 148a that is aligned with the knife slot 30a of the channel member 30 and is positioned distally of the fin 96 of the actuation sled 84 of the actuation sled assembly 44. The stop member 148 of the lockout member 140 also includes a lance 152 that extends distally between the two legs 150 of the lockout member 140 along the knife slot 30a. The lance 152 may angle slightly downwardly in the distal direction towards the knife slot 30a of the channel member 30. In aspects of the disclosure, each of the legs 150 of the lockout member 140 includes a shoulder 156 that abuts a proximal surface of the overhang 144 of the channel member 30.

In the open position of the stapling device 10 (FIG. 1), the working member 114 is positioned proximally of the actuation sled assembly 44 and proximally of the ramps 142. FIGS. 11 and 12 illustrate the tool assembly 16 of the stapling device 10 (FIG. 1) in a clamped position. When the drive assembly 110 is moved in the direction of arrow "A" in FIG. 12 from the retracted position to a clamped position, the working member 114 moves into abutting relation with the actuation sled assembly 44 and the first beam 118 of the working member 114 moves over the ramps 142 of the channel member 30 to pivot the cartridge assembly 26 in the direction of arrow "B" in FIG. 11 from the open position to the clamped position. In the clamped position, the knife blade 106 of the knife 86 is received within the distally facing concavity 132 in the vertical strut 122 of the working member 114 of the drive assembly 110 such that the working member 114 of the drive assembly 110 is in abutting relation to the actuation sled assembly 44.

Figure 13:
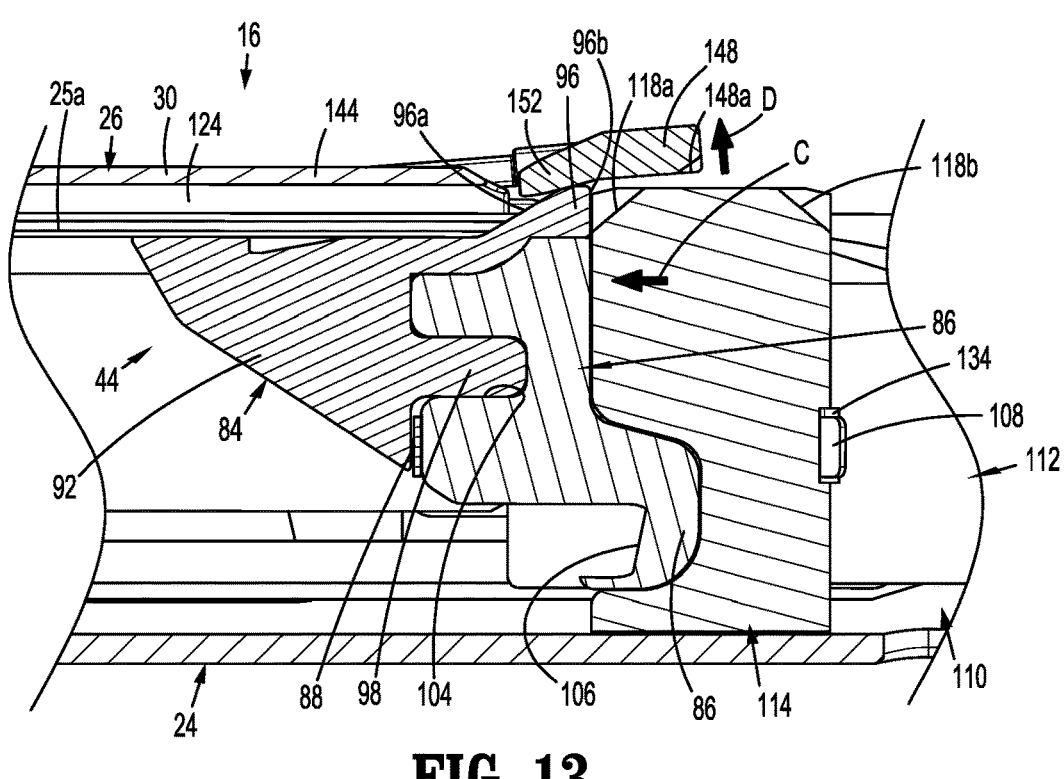
FIG. 13 is a cross-sectional view taken through the proximal portion of the tool assembly shown in FIG. 11 as the drive assembly begins to move through a firing stroke.

FIG. 13 illustrates the proximal portion of the tool assembly 16 as the drive assembly 110 is advanced in the direction of arrow "C" from the clamped position towards the advanced position to eject staples 48 from the cartridge body 42 of the staple cartridge 28. As the drive assembly 110 is advanced from the clamped position towards the advanced position, the working member 114 advances the actuation sled assembly 44 from the sled retracted position towards the sled advanced position. As the actuation sled assembly 44 begins to advance in the direction of arrow "C", the angled distal cam surface 96a of the fin 96 of the actuation sled 84 engages the angled cam surface 148a on the stop member 148 of the lockout member 140 and urges the stop member 148 upwardly in the direction of arrow "D" to allow the actuation sled assembly 44 and the working member 114 of the drive assembly 110 to pass under the lockout member 140. Once the working member 114 of the drive assembly 110 moves distally past the lockout member 140, the working member 114 is free to move to its advanced position to move the actuation sled assembly 44 to the sled advanced position to eject the staples 48 (FIG. 3) from the cartridge body 42 of the staple cartridge 28. It is noted that when the actuation sled assembly 44 moves towards the sled advanced position, the curved portion 88b of the retraction link 88 moves from within the recess 91 (FIG. 18A) into the knife slot 52 and is deformed inwardly such that the bend or protrusion 108 of the retraction link 88 is received in the opening 134 in the vertical strut 122 of the working member 114. When this occurs, the actuation sled assembly 44 is coupled to the working member 114 such that the actuation sled assembly 44 will be retracted with the working member 114 after firing is completed.

Figure 14:
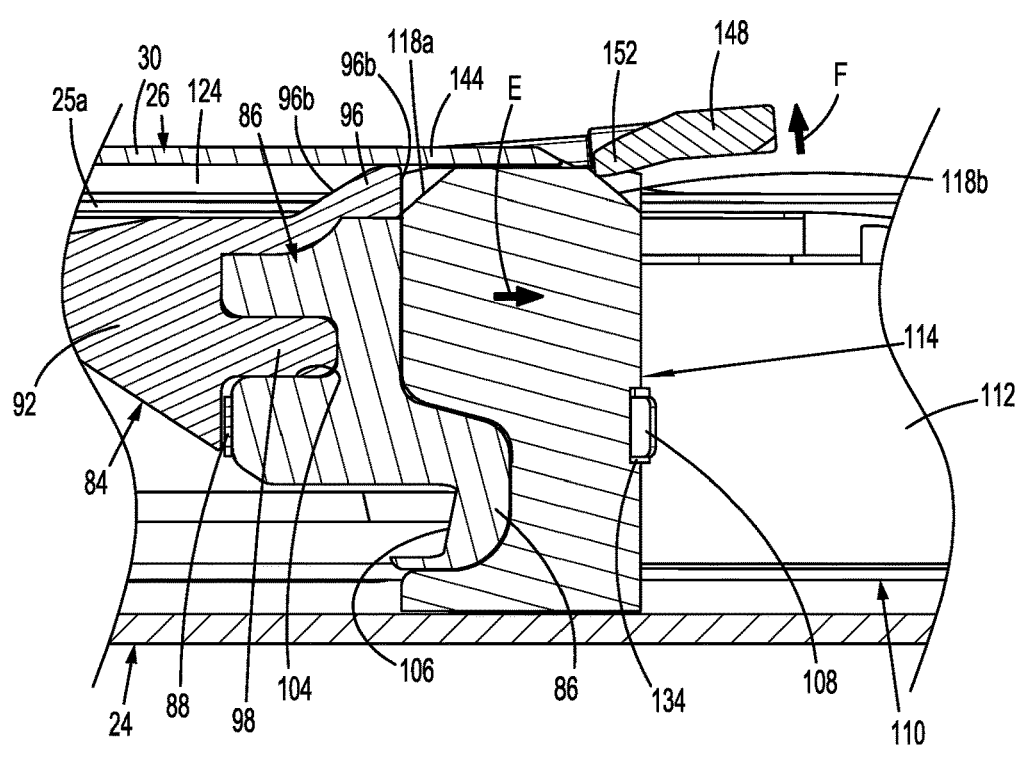
FIG. 14 is a cross-sectional view taken through the proximal portion of the tool assembly as the drive assembly is returned towards the retracted position after the firing stroke.
Figure 15:
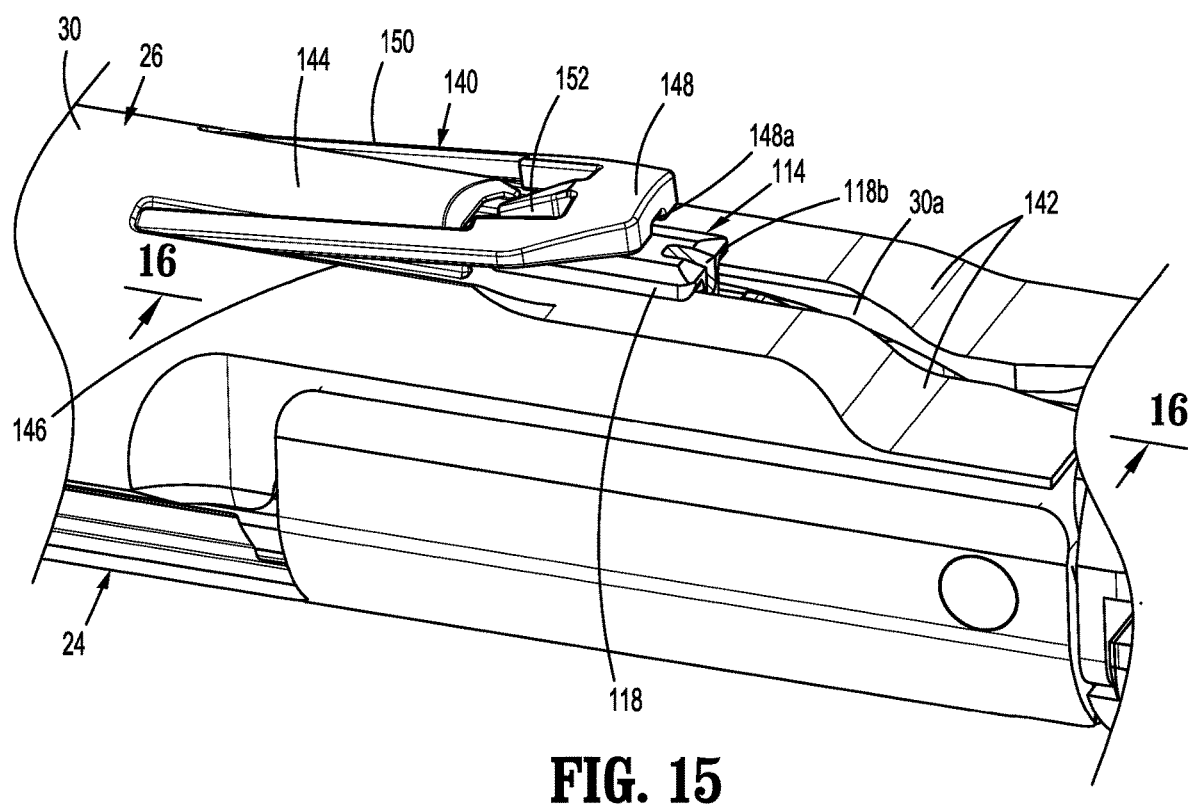
FIG. 15 is a perspective view of the proximal portion of the tool assembly shown in FIG. 11 as the drive assembly moves closer to the retracted position after the firing stroke.
Figure 16:
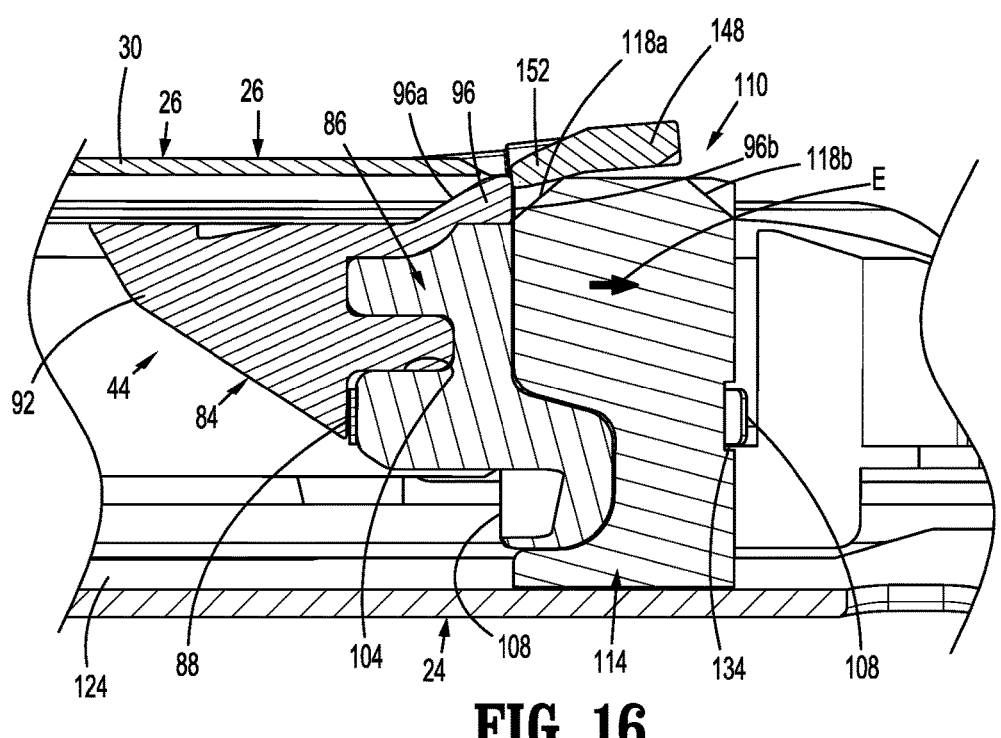
FIG. 16 is a cross-sectional view taken along section line 16-16 of FIG. 15.
Figure 17:
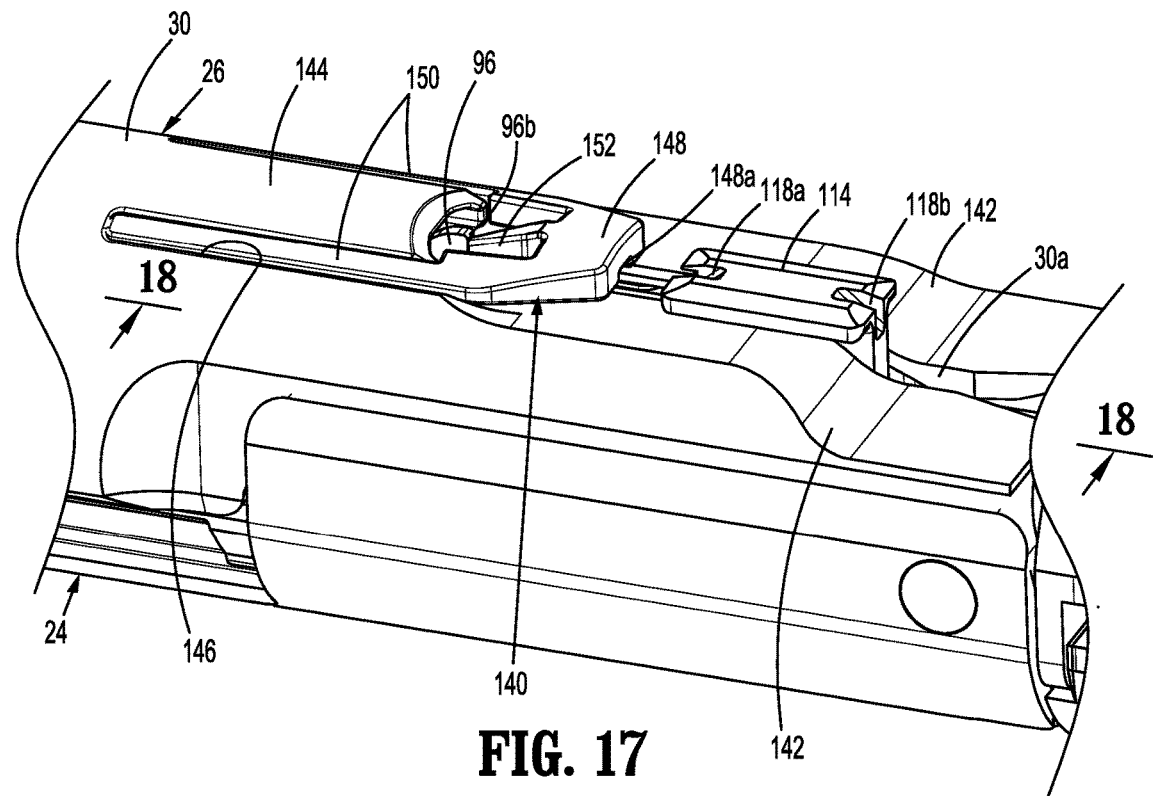
FIG. 17 is a perspective view of the proximal portion of the tool assembly shown in FIG. 11 with the drive assembly in the retracted position after the firing stroke.
Figure 18:
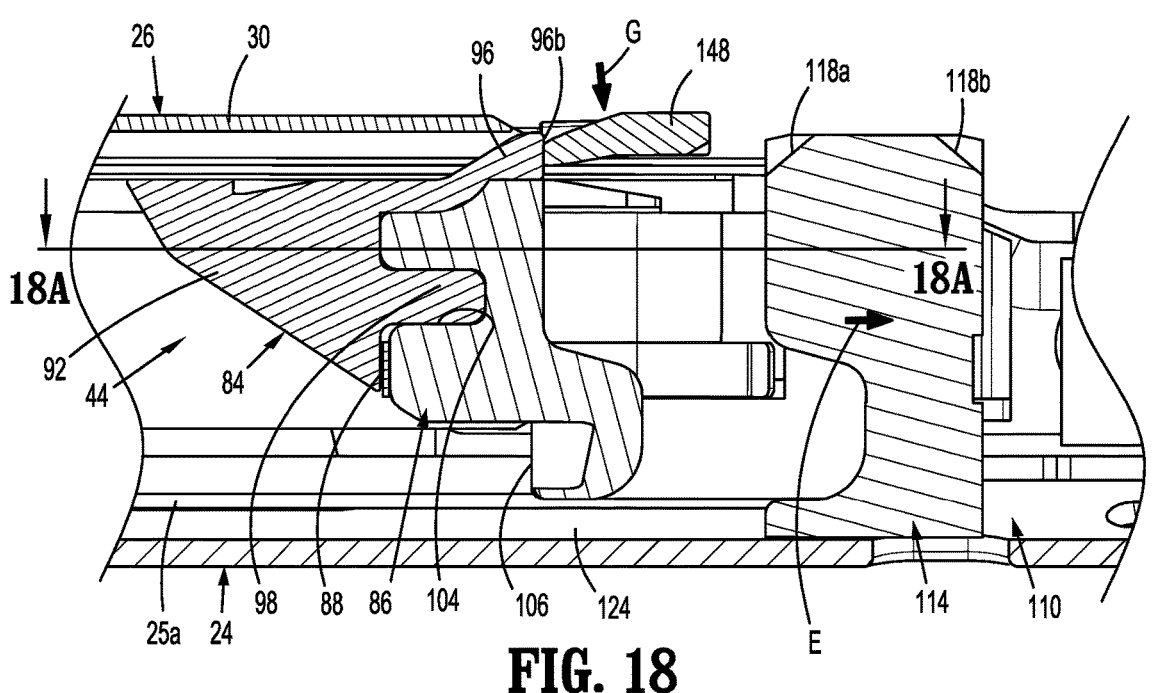
FIG. 18 is a cross-sectional view taken along section line 18-18 of FIG. 17.
Figure 18A:
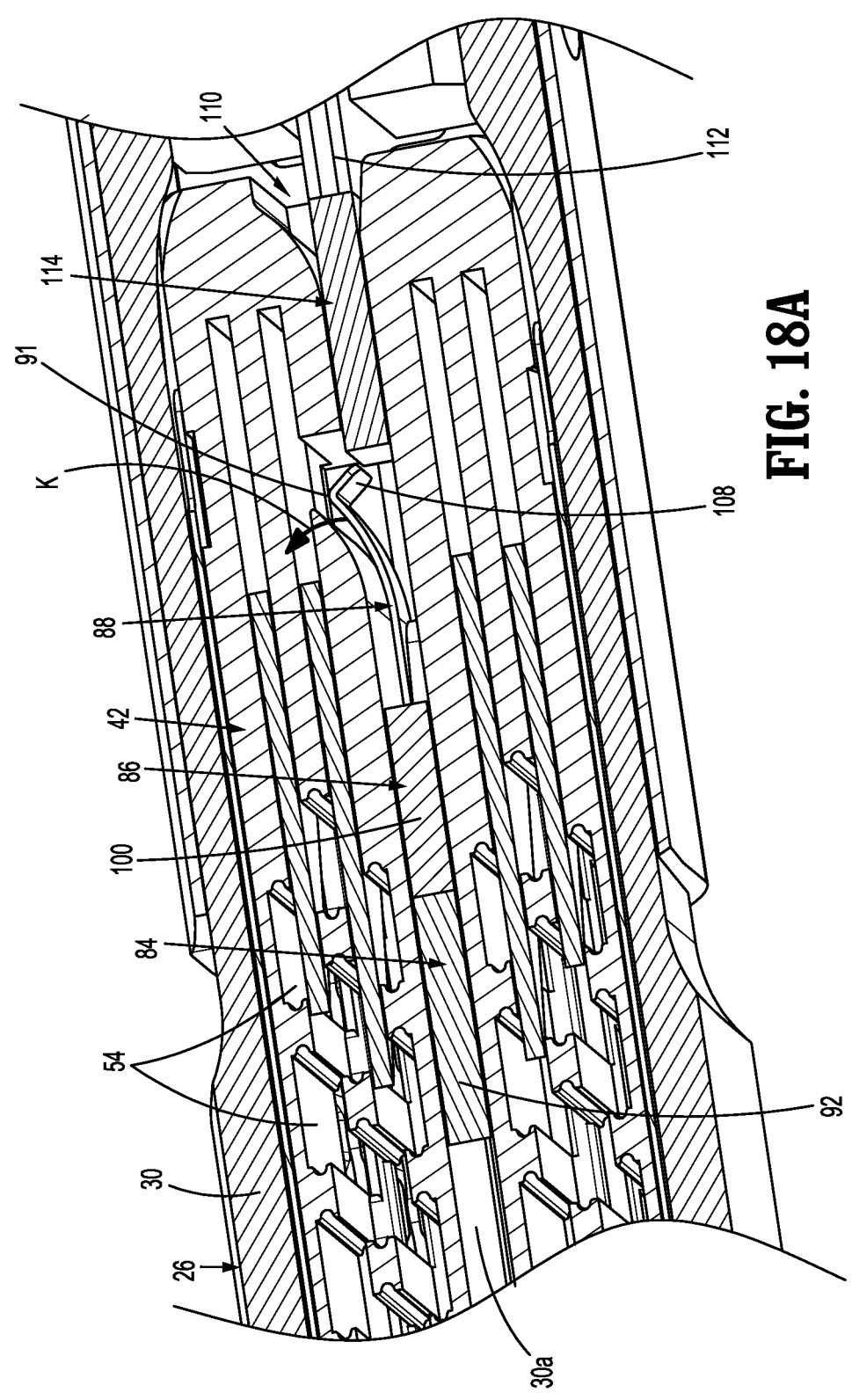
FIG. 18A is a cross-sectional view taken along section line 18A-18A of FIG. 18.

FIGS. 14-18A illustrate the tool assembly 16 as the working member 114 of the drive assembly 110 and the actuation sled assembly 44 are retracted in the direction of arrow "E" in FIG. 16 after the stapling device 10 (FIG. 1) has been fired. When the proximally facing cam surface 118b of the first beam 118 of the working member 114 engages the lance 152 of the stop member 148 of the lockout member 140, the stop member 148 is urged upwardly in the direction of arrow "F" in FIG. 14 to allow the working member 114 to pass proximally under the lockout member 140 and return to its retracted position (FIGS. 14-16). When the drive assembly 110 returns to the clamped position and the curved portion 88b of the retraction link 88 aligns with the recess 91 (FIG. 18A) in the cartridge body 42, the curved portion 88b of the retraction link 88 returns to the non-deformed configuration in the direction of arrow "K" in FIG. 18A and moves back into the recess 91 in the cartridge body 42. When the working member 114 is retracted past the stop member 148 of the lockout member 140, the lance 152 of the lockout member 140 will move downwardly in the direction of arrow "G" in FIG. 18 and engage the stop surface 96b of the fin 96 of the actuation sled assembly 44 to prevent further retraction of the actuation sled assembly 44. In that respect, the distally facing cutout 118a of the first beam 118 of the working member 114 is positioned adjacent the proximal surface of the fin 96 and allows the lance 152 to engage the stop surface 96*b* of the fin 96 to obstruct further proximal movement of the actuation sled assembly 44. The working member 114 of the drive assembly 110 will continue to move from the clamped position to the retracted position independently of the actuation sled assembly 44 (FIGS. 17 and 18).

Figure 19:
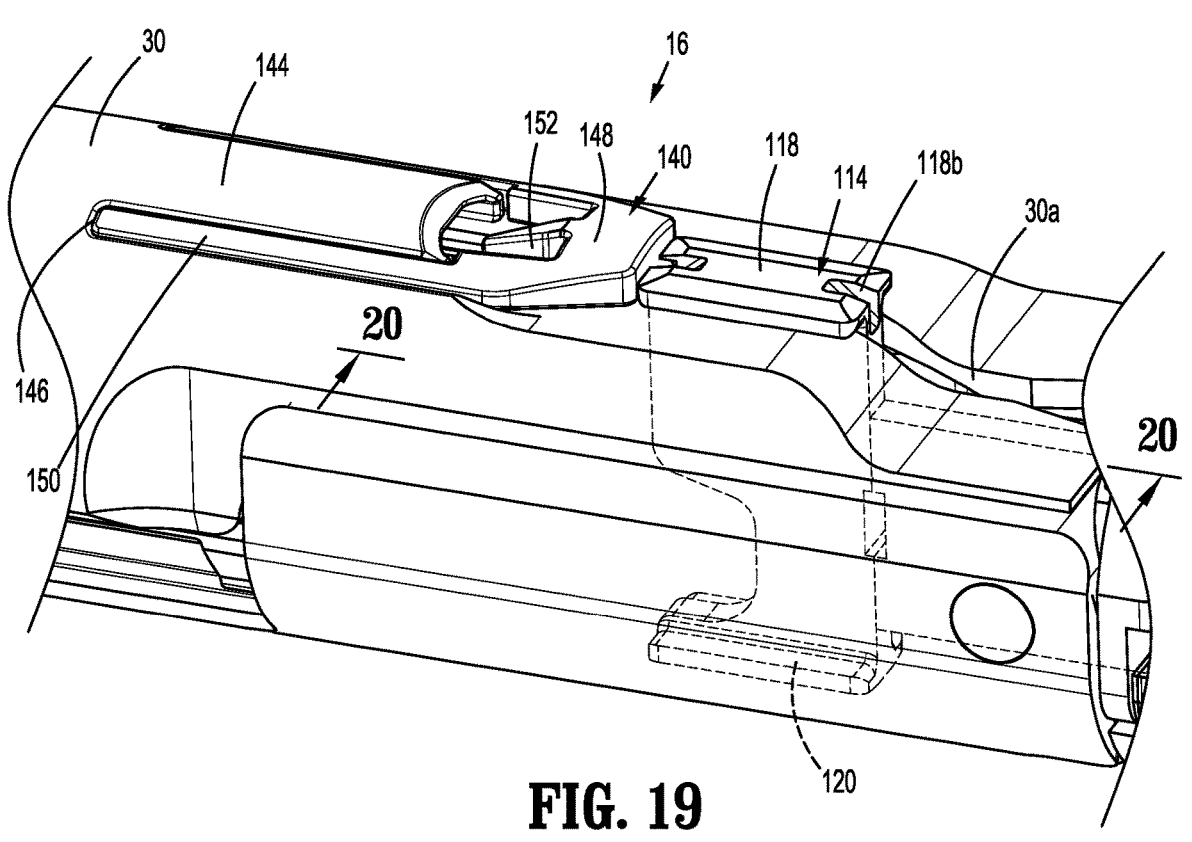
FIG. 19 is a side perspective view of the tool assembly of the stapling device shown in FIG. 1 with the tool assembly in a clamped position with no actuation sled assembly present in the staple cartridge.
Figure 20:
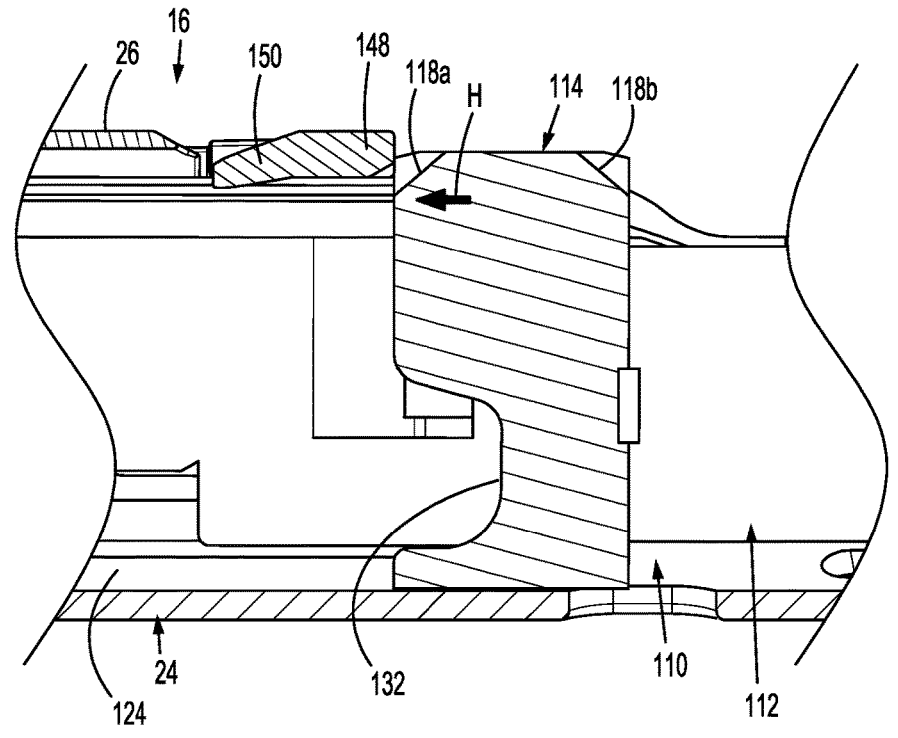
FIG. 20 is a cross-sectional view taken along section line 20-20 of FIG. 19.

FIGS. 19 and 20 illustrate the tool assembly 16 of the stapling device 10 (FIG. 1) when there is an attempt to fire the stapling device 10 when the actuation sled assembly 44 is not present in the proximal portion of the staple cartridge 28. This may occur when the staple cartridge 28 was manufactured improperly without an actuation sled assembly 44 or when there is an attempt to fire the stapling device 10 with a spent staple cartridge 28. When the working member 114 is advanced in the direction of arrow "H" in FIG. 20 without the actuation sled assembly 44 present in the proximal portion of the staple cartridge 28, the first beam 118 of the working member 114 engages the proximal face of the stop member 148 of the lockout member 140 to prevent advancement of the working member 114 from the clamped position towards the advanced position. This prevents advancement of the knife 86 when staples 48 and/or the actuation sled 84 are not present in the staple cartridge 28.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
an elongate body having a proximal portion and a distal portion;
a tool assembly supported on the distal portion of the elongate body, the tool assembly including:
an anvil assembly having a staple forming surface that defines a first knife slot; and
a cartridge assembly coupled to the anvil assembly to facilitate movement of the tool assembly between open and clamped positions, the cartridge assembly including a channel member and a staple cartridge, the channel member having side walls and a bottom wall defining a channel, the bottom wall defining a second knife slot, the staple cartridge supported within the channel of the channel member and including a cartridge body, staples, pushers, and an actuation sled assembly, the cartridge body having a tissue engaging surface and defining a third knife slot and staple receiving slots positioned on each side of the third knife slot, the staples received in the staple receiving slots, the actuation sled assembly movable within the cartridge body from a sled retracted position to a sled advanced position to eject the staples from the staple receiving slots of the cartridge body, the actuation sled assembly including an actuation sled and a knife secured to the actuation sled, the actuation sled having a fin that extends through the second knife slot to a position outwardly of the channel, the knife including a knife blade having a cutting edge positioned within and extending above the tissue engaging surface of the cartridge body;
a drive assembly including a working member, the working member positioned proximally of the actuation sled assembly and movable through the cartridge body between retracted and advanced positions to advance the actuation sled assembly from the sled retracted position to the sled advanced position; and
a lockout member supported on an outer surface of the channel member, the lockout member being movable from a first position obstructing movement of the working member from the retracted position to the advanced position to a second position allowing movement of the working member from the retracted position to the advanced position,
wherein the fin of the actuation sled is positioned to engage the lockout member when the actuation sled assembly is moved from the sled retracted position towards the sled advanced position to move the lockout member from the first position to the second position.

2. The surgical stapling device of claim 1, wherein the lockout member includes a stop member that extends across the second knife slot, and the fin of the actuation sled is positioned to engage the stop member to move the lockout member from the first position to the second position.

3. The surgical stapling device of claim 2, wherein the fin has an angled distal cam surface and a proximal stop surface, the angled distal cam surface configured to move the lockout member from the first position to the second position.

4. The surgical stapling device of claim 3, wherein the lockout member includes a lance that extends distally from the stop member, the lance positioned to engage the proximal stop surface of the fin to prevent movement of the actuation sled assembly to the sled retracted position.

5. The surgical stapling device of claim 4, wherein the actuation sled assembly includes a retraction link that is moveable from a first position to a second position in response to movement of the actuation sled assembly from the sled retracted position towards the sled advanced position to couple the actuation sled assembly to the working member of the drive assembly.

6. The surgical stapling device of claim 5, wherein the retraction link includes a protrusion, and the drive assembly defines an opening, the protrusion received within the opening when the retraction link is in the second position.

7. The surgical stapling device of claim 6, wherein the working member includes first and second beams and a vertical strut connecting the first beam to the second beam, the vertical strut movable through the first, second, and third knife slots as the working member moves between the retracted and advanced positions.

8. The surgical stapling device of claim 7, wherein the first beam includes a proximally facing cam slot that is positioned to engage the lance when the working member moves from the advanced position to the retracted position to move the lockout member from the first position to the second position.

9. The surgical stapling device of claim 8, wherein the first beam includes a distally facing cutout that is positioned adjacent the fin of the actuation sled to allow the lance to engage the stop surface of the fin.

10. The surgical stapling device of claim 1, further including a handle assembly coupled to the proximal portion of the elongate body.

11. A tool assembly comprising:

an anvil assembly having a staple forming surface that defines a first knife slot; and a cartridge assembly coupled to the anvil assembly to facilitate movement of the tool assembly between open and clamped positions, the cartridge assembly including a channel member and a staple cartridge, the channel member having side walls and a bottom wall defining a channel, the bottom wall defining a second knife slot, the staple cartridge supported within the channel of the channel member and including a cartridge body, staples, pushers, and an actuation sled assembly, the cartridge body having a tissue engaging surface and defining a third knife slot and staple receiving slots positioned on each side of the third knife slot, the staples received in the staple receiving slots, the actuation sled assembly movable within the cartridge body from a sled retracted position to a sled advanced position to eject the staples from the staple receiving slots of the cartridge body, the actuation sled assembly including an actuation sled and a knife secured to the actuation sled, the actuation sled having a fin that extends through the second knife slot to a position outwardly of the channel, the knife including a knife blade having a cutting edge positioned within and extending above the tissue engaging surface of the cartridge body;

a drive assembly including a working member, the working member positioned proximally of the actuation sled assembly and movable through the cartridge body between retracted and advanced positions to advance the actuation sled assembly from the sled retracted position to the sled advanced position; and a lockout member supported on an outer surface of the channel member, the lockout member being movable from a first position obstructing movement of the working member from the retracted position to the advanced position to a second position allowing movement of the working member from the retracted position to the advanced position, wherein the fin of the actuation sled is positioned to engage the lockout member when the actuation sled assembly is moved from the sled retracted position towards the sled advanced position to move the lockout member from the first position to the second position.

12. The tool assembly of claim 11, wherein the lockout member includes a stop member that extends across the second knife slot, and the fin of the actuation sled is positioned to engage the stop member to move the lockout member from the first position to the second position.

13. The tool assembly device of claim 12, wherein the fin has an angled distal cam surface and a proximal stop surface, the angled distal cam surface configured to move the lockout member from the first position to the second position.

14. The tool assembly of claim 13, wherein the lockout member includes a lance that extends distally from the stop member, the lance positioned to engage the proximal stop surface of the fin to prevent movement of the actuation sled assembly to the sled retracted position.

15. The tool assembly of claim 14, wherein the actuation sled assembly includes a retraction link that is moveable from a first position to a second position in response to movement of the actuation sled assembly from the sled retracted position towards the sled advanced position to couple the actuation sled assembly to the working member of the drive assembly.

16. The tool assembly of claim 15, wherein the retraction link includes a protrusion, and the drive assembly defines an opening, the protrusion received within the opening when the retraction link is in the second position.

17. The tool assembly of claim 16, wherein the working member includes first and second beams and a vertical strut connecting the first beam to the second beam, the vertical strut movable through the first, second, and third knife slots as the working member moves between the retracted and advanced positions.

18. The tool assembly of claim 17, wherein the first beam includes a proximally facing cam slot that is positioned to engage the lance when the working member moves from the advanced position to the retracted position to move the lockout member from the first position to the second position.

19. The tool assembly of claim 18, wherein the first beam includes a distally facing cutout that is positioned adjacent the fin of the actuation sled to allow the lance to engage the stop surface of the fin.

20. A cartridge assembly comprising:

a channel member having side walls and a bottom wall defining a channel, the bottom wall defining a first knife slot;

a staple cartridge supported within the channel of the channel member and including a cartridge body, staples, pushers, and an actuation sled assembly, the cartridge body having a tissue engaging surface and defining a second knife slot and staple receiving slots positioned on each side of the second knife slot, the staples received in the staple receiving slots, the actuation sled assembly movable within the cartridge body from a sled retracted position to a sled advanced position to eject the staples from the staple receiving slots of the cartridge body, the actuation sled assembly including an actuation sled and a knife secured to the actuation sled, the actuation sled having a fin that extends through the first knife slot to a position outwardly of the channel, the knife including a knife blade having a cutting edge positioned within and extending above the tissue engaging surface of the cartridge body; and a lockout member supported on an outer surface of the channel member of the cartridge assembly, the lockout member having a stop member that extends across the first knife slot, the lockout member being movable from a first locked position to a second unlocked position in response to movement of the actuation sled assembly from the sled retracted position towards the sled advanced position.

* * * * *